United States Patent
Lucia et al.

(10) Patent No.: US 8,404,468 B2
(45) Date of Patent: Mar. 26, 2013

(54) **EFFICIENT ASTAXANTHIN PRODUCTION STRAINS DERIVED FROM *HAEMATOCOCCUS PLUVIALIS***

(75) Inventors: Martin Lucia, Seville (ES); Irina Obraztsova, Seville (ES); Baldomero F. Cordero, Bormujos Sevilla (ES); Angeles M. Vargas, Dos-Hermanes Sevilla (ES); Albrecht Weiss, Langenfeld (DE); Bernhard Gutsche, Hilden (DE); Wilhelm Johannisbauer, Erkrath (DE); Herminia Rodriguez, Seville (ES)

(73) Assignee: Cognis IP Management GmbH, Duesseldorf (DE)

( * ) Notice: Subject to any disclaimer, the term of this patent is extended or adjusted under 35 U.S.C. 154(b) by 385 days.

(21) Appl. No.: 12/601,471

(22) PCT Filed: May 14, 2008

(86) PCT No.: PCT/EP2008/003850
§ 371 (c)(1),
(2), (4) Date: Jul. 20, 2010

(87) PCT Pub. No.: WO2008/141757
PCT Pub. Date: Nov. 27, 2008

(65) Prior Publication Data
US 2010/0285557 A1     Nov. 11, 2010

(30) Foreign Application Priority Data
May 23, 2007 (EP) .................... 07010258
Feb. 26, 2008 (DE) .................... 10 2008 010 989

(51) Int. Cl.
C12P 1/02     (2006.01)
C12N 15/01    (2006.01)
C12N 1/15     (2006.01)

(52) U.S. Cl. .................... 435/171; 435/254.11; 435/441

(58) Field of Classification Search ................ None
See application file for complete search history.

(56) References Cited

FOREIGN PATENT DOCUMENTS

| EP | 1229126 A1 | 8/2002 |
|---|---|---|
| WO | 91/18108 A1 | 11/1991 |
| WO | 92/22648 A1 | 12/1992 |
| WO | 01/62894 A2 | 8/2001 |

OTHER PUBLICATIONS

Namthip Chumpolkulwong et al:"Isolation and characterization of compactin resistant mutants of an astaxanthin synthesizing green alga *Haematococcus pluvialis*" Biotechnology letter, vol. 19, No. 3, pp. 299-302.,Mar. 1997.
Young Chen et al;"Screening and characterization of astaxanthin-hyperproducing mutants of *Haematococcus pluvialis*"; Biotechnology Letters vol. 25, pp. 527-529, (2003).
Park et al.: "Enhancement of Astaxanthin Production of *Haematococcus pluvialis* by Mutation"; Korean Journal of Microbiology and Biotechnology,vol. 34,No. 2, pp. 136-142(2006,) xp008084674.
Jin,Eonseon et al; "Secondary carotenoid Accumulation in *Haematococcus*(Chlorophyceae):Biosynthesis, Regulation,and Biotechnology";Korean Journal of Microbiology and Biotechnology, vol. 16(6), pp. 821-831, (2006) xp002454322.
Sheng-Bing Wang et al; "Isolation and proteomic alalysis of cell wall-deficient *Haematococcus pluvialis* mutants"; Proteomic journal vol. 5, pp. 4839-4851 (2005) xp002454408.
Esperanza Del Rio et al; "Efficient One-Step Production of Astaxanthin by the Microalga *Haematococcus pluvialis* in Continuos Culture" Biotechnology and Bioengineering, vol. 91, pp. 808-815 (2005) xp002454957.
Abdolmajid Lababpour et al; Fed-batch cultivation of *Haematococcus pluvialis* under illumination with LEDs for production of astaxanthin; Journal of Biotechnology vol. 118(S1) pp. 116, (Aug. 2005) xp002454321.
Jens Steinbrenner et al; "Transformation of the Green Alga *Haematococcus pluvialis* with a Phytoene Desaturase for Accelerated Astaxanthin Biosynthesis" Applied and Environmental microbiology,vol. 72. pp. 7477-7484, Dec. 2006 xp008076283.
Martin Obraztsova et al; "Mutagenesis of *Haematococcus pluvialis*" European Society of Microbioalga Biotechnology, vol. 22 pp. 1. Jun. 2007 xp002454323.
Agus Eko Tjahjono et al; "Isolation of resistant Mutants against Carotenoid Biosynthesis Inhibitors for a Green Alga *Haematococcus pluvialis* and their hybrid Formation by Protoplast Fusion for Breeding of Higher Astaxanthin producers" Journal of Fermentation and Bioengineering. vol. 77. No. 4, pp. 352-357. (1994).
Park, Bok-Jun et al., "Enhancement of Astaxanthin my Microalga *Haematococcus pluvialis* Through Mutagenesis", *Kor. J. Microbiol. Biotechnol.*, vol. 34, No. 2 XP008084674 2006, 136-142.

*Primary Examiner* — Kagnew H Gebreyesus
(74) *Attorney, Agent, or Firm* — Servilla Whitney LLC

(57) ABSTRACT

The present invention pertains to a method for the efficient production of carotenoids. In particular, the present invention is directed to a method for producing carotenoid and carotenoid-containing cells, especially astaxanthin and astaxanthin-containing cells, by generating mutant microorganisms belonging to the photoautotrophic algae of the Class Chlorophyceae and culturing same. The present invention further relates to methods of generating microorganisms producing high yields of carotenoids, in particular astaxanthin, products containing said microorganisms or said carotenoids, and the use of said carotenoids produced by the microorganisms according to the present invention and deposited mutant strains generated from said microorganisms.

12 Claims, No Drawings

EFFICIENT ASTAXANTHIN PRODUCTION STRAINS DERIVED FROM *HAEMATOCOCCUS PLUVIALIS*

CROSS REFERENCE TO RELATED APPLICATIONS

This application is the National Stage entry of PCT/EP2008/003850, filed May 14, 2008, which claims priority to European Patent application number 07010258, filed May 23, 2007, and which claims priority to German Patent application number 10 2008 010 989.4, filed Feb. 26, 2008, all of which are incorporated herein by reference in their entireties.

FIELD OF THE INVENTION

The present invention pertains to a method for the efficient microbiological production of carotenoids. More specifically, the present invention is directed to a method for producing carotenoid and carotenoid-containing cells, in particular astaxanthin and astaxanthin-containing cells, by generating mutant microorganisms belonging to the photoautotrophic algae of the Class Chlorophyceae and culturing same.

The present invention further relates to methods of generating microorganisms producing high yields of carotenoids, in particular astaxanthin, products containing said microorganisms or said carotenoids, and the use of said carotenoids produced by the microorganisms according to the present invention and deposited mutant strains of said microorganisms.

BACKGROUND OF THE INVENTION

The carotenoid compounds of the present invention comprise natural pigments. It is known that carotenoids are useful additives in manufacturing of food products, feed products, cosmetics or pharmaceuticals.

The natural pigments of carotenoids are responsible for many of the yellow, orange, red or reddish colours seen in living organisms. In particular, astaxanthin is responsible for the red colour of crustaceae, molluscs and salmons, which cannot synthesize astaxanthin de novo and therefore it is necessary to add it to the diets of these animals.

Carotenoids are widely distributed in nature comprising plant and animal kingdoms. The colour varies dependent on the lengths of the chromophore and the type of the oxygen-containing groups attached. Carotenoid pigment formation is known from yeasts, certain bacteria, fungi and unicellular algae.

The carotenoids have in principle two biological functions. They serve as light-harvesting pigments in photosynthesis and they protect against photo oxidative damage caused by active oxygen species such as $O_2·$, $H_2O_2$ or $OH·$, which are continuously generated in living cells.

Furthermore, carotenoids can absorb photons and transfer the energy to chlorophyll, thus assisting in the harvesting of sunlight.

It is further known that β-carotene, a precursor of astaxanthin, protects against radiation by absorption of energy in the blue region of the light spectrum. It is suggested that β-carotene in the body may protect against cancer and that it also functions as a precursor of vitamin A in mammals so that it is involved in provitamin A activity.

It has been shown that carotenoids, in particular astaxanthin, protect the skin from the damaging effects of ultraviolet radiation and ameliorate age-related macular degeneration. In addition, astaxanthin increases high density lipoproteins and protects against cardiovascular diseases.

The function of astaxanthin as a powerful antioxidant in animals is well known. Astaxanthin is a strong inhibitor of lipid peroxidation and has been shown to play an active role in the protection of biological membranes from oxidative injury. According to recent investigations it has been scrutinized that astaxanthin also shows chemo-preventive effects and reduce the incidence of chemically induced urinary bladder cancer in mice. In addition it has also been demonstrated that astaxanthin exerts immunomodulating effects by enhancing antibody production. These preliminary results suggest that astaxanthin could play an important role in cancer and tumor prevention, as well as eliciting a positive response from the immune system, thus making astaxanthin to a promising candidate in medicine and for the pharmaceutical industry.

Besides these physiological and medical functions, astaxanthin further plays or may play a role as antioxidant, hormone precursor, in reproduction, in growth and maturation.

Because of the powerful antioxidant activity of astaxanthin it is starting to be used in the human health-food sector. The antioxidant activities of astaxanthin have been shown to be approximately ten times greater than other carotenoids, such as zeaxanthin, lutein, cantaxanthin and β-carotene, and over 500 times greater than α-tocopherol, also known as vitamin E.

Astaxanthin is utilized mainly as nutritional supplement, which provides pigmentation in a wide variety of aquatic animals. In Far East it is used also for feeding poultry to yield a typical pigmentation of chicken. It is also a desirable and effective non-toxic colouring for the food industry and is valuable for cosmetics. It has also been shown that astaxanthin is a potent antioxidant in humans and thus is a desirable food additive.

Many researchers remark the vital role that especially astaxanthin plays in the physiology and in overall health, and suggest that astaxanthin is an essential nutrient that should be included in all aquatic diets at a minimum level of 5-10 parts per million (ppm).

While astaxanthin is a natural nutritional component, it can be found as a food supplement. The supplement is intended for human, animal, and aquaculture consumption. The commercial production of astaxanthin comes from both natural and synthetic sources. The FDA approved astaxanthin as a food colouring or colour additive for specific uses in animal and fish foods. The European Commission considers it as food dye within the E number system (E161j).

Therefore, Carotenoids, especially natural born astaxanthin, have a high industrial value as a safe natural food and feed additive, such as a colour improver, for fishes such as salmon, trout or red sea bream. In addition, it is promising as an additive in cosmetics and pharmaceuticals. Hence, there is an increasing interest in developing biological production of carotenoids, especially astaxanthin.

Until recently, the commercial interest focussed on the yeast *Phaftia rhodozyma*, but astaxanthin contents are low (0.3-0.5% dry weight) even after considerable strain improvement efforts. Shrimps shell waste is another potential source of astaxanthin, but direct use of the material is very low in astaxanthin (0.0025% dry weight). As a result, the quantities required in the feeds for efficient pigmentation add deleterious bulk and ash to the final feeds. The composition of astaxanthin esters in *Haematococcus* is similar to that of crustaceans, the natural dietary source of salmons. Moreover, all of the free astaxanthin and its esters in *Haematococcus* have 3S,3'S chirality, the same as in free salmonids, whereas *Phaffia* contains 3R,3'R astaxanthin and the synthetic one is a mixture of three isomers.

Currently, most of the astaxanthin is supplied, mainly for aquaculture, through chemical synthesis. However, because astaxanthin is a complex molecule and the synthesis is difficult. Therefore, the industrial use of carotenoids is hampered by the fact that synthetic carotenoid production, in particular the synthetic astaxanthin production, as well as the process for isolating natural astaxanthin are expensive, laborious and subject to seasonal variations.

A process for producing carotenoids, such methods as chemical synthesis, production by microorganisms, and extraction from natural products or sources are known in the art. As processes of chemical synthesis, the conversion of β-carotene and the synthesis from $C_{15}$-phosphonium salts is also known for a long time.

As processes for producing β-carotene synthesis from β-ionone and extraction from green, yellow or red vegetables such as carrots, potatoes or pumpkins is known.

Carotenoids obtained by microorganisms, in particular astaxanthin obtained by microorganisms such as algae, have many advantages in comparison to the synthetic one, such as better retention in the fish gut, and a better acceptance by the consumers. In addition, regulations on the use of synthetic dyes in the food, cosmetic and pharmaceutical industry are currently very stringent. In this regard, *Haematococcus* algae meal has been approved in Japan, Europe and USA as a natural food colour and as a pigment for fish feeds.

The above-described production processes have various severe problems. Firstly, safety is not assured for the synthesized products; secondly, the production by microorganisms is low in productivity; thirdly, extraction from natural products or sources requires high costs. In particular, the latter is especially valid for astaxanthin since extraction from natural sources such as krill or crawfish requires high costs since the content of astaxanthin is extremely small and yet the extraction is difficult and time consuming. In addition, astaxanthin producing microorganisms are generally characterized in that they have a low growth rate, produce only small amounts of astaxanthin and have a robust cell wall that makes the extraction of the carotenoid difficult and thus not economical.

In particular, in the case of the green alga *Haematococcus pluvialis* the majority of these problems are combined. In addition to its extremely low growth rate, it is known that the cultures of this microorganism are easily contaminated.

In contrast to natural occurring astaxanthin the synthetic substance consists of a mixture of the (3S,3'S)-, (3S,3'R)- and (3R,3'R)-isomers and is commercially available under the trade name Carophyll® Pink.

Natural (3S,3'S) astaxanthin is limited in availability. Currently, in spite of the above-mentioned disadvantages and because of the lack of any alternatives it is commercially extracted from crustacea species and *Haematococcus pluvialis*.

However, the success of commercial mass production of carotenoids, especially of astaxanthin by *Haematococcus pluvialis*, is hampered by a relatively low productivity of the cultures. This raises the production costs in such a way that in particular *Haematococcus* astaxanthin cannot compete on price against the synthetic pigment, which in turn consists of a mixture of isomers and laws or rules limit its commercial application as set forth supra.

There are several articles in the literature about mutants of *Haematococcus pluvialis*, but none of them describe any successful results as to the production of a carotenoid with high yield. For example, Tjahjono et al. used ethyl methansulfonate (EMS) to mutagenized *Haematococcus pluvialis* cells and three carotenoid biosynthesis inhibitors (norflurazon, fluridone and nicotine) for selection of resistant colonies. Some resistant mutants were obtained, but no one exhibited an enhanced volumetric content of carotenoids. The work consists in isolation of resistant mutants from the green alga *Haematococcus pluvialis* and their hybrid formation by protoplast fusion for breeding of higher astaxanthin producers. The fusion of protoplasts produces usually very unstable organisms that have to be kept in selective medium, in addition the growth of the mutants was much lower than the wild strains (Tjahjono, A. E. et al. J. Ferment. Bioeng. 77: 352-357, 1994).

In another article EMS and UV light were used for mutagenesis of *Haematococcus pluvialis* and compactin was used for selection of the mutants. Data of only two resistant mutants are presented, which have 1.4 and 2.0 fold higher astaxanthin content per cell than the wild type. However, the mutants grew slower and attained lower cell densities than the wild strain and no enhancement of the volumetric content could be measured in the mutant strains (Chumpolkulwong N. et al., Isolation and characterization of compactin resistant mutants of an astaxanthin synthesizing green alga *Haematococcus pluvialis*. Biotechnol. Lett. 19: 299-302, 1997).

In a more recent study that was published 6 to 9 years later from the former studies UV light or EMS induced mutagenesis has been used in two rounds and mutant selection on nicotine, diphenylamine, fluridone or norflurazon supplemented medium. The first round of mutagenesis gave rise to 1.6 and 1.7 times (w/w) more astaxanthin-rich mutants by screening with nicotine. In the second round of mutagenesis one of these two mutants was improved somewhat more to reach 2.1-fold increase in astaxanthin content in comparison with the wild strain. However, the growth rate of the mutants was much lower than that of the wild strain (Chen Y., et al. Screening and characterization of astaxanthin-hyperproducing mutants of *Haematococcus pluvialis*, Biotech. Lett. 25: 299-302, 2003).

For the reasons mentioned above the known processes for industrial production of astaxanthin from algae, especially from *Haematococcus pluvialis*, seems to be impracticable or are at least very difficult and full of disadvantages. Moreover, the known processes are not attractive due to high costs, low contents in natural sources, laborious extraction processes with unsatisfying or disappointing results and lack of constant availability of the resources.

Hence, it is desirable to find a method or process for producing and providing carotenoid compounds or carotenoid pigments, a method for generating microorganisms producing high quantities of carotenoid pigments or cells containing high quantities of carotenoid pigments, respectively, as well as inexpensive means in order to make these carotenoids attractive and economical for industrial productivity and industrial application.

In particular, it is desirable to find an inexpensive, economical and non-laborious source for the production of (3S, 3'S) astaxanthin for commercial or industrial and medical purposes It is therefore an object of the present invention to provide an effective and economically advantageous method for producing a carotenoid, in particular to provide an effective and economically advantageous method for the production of astaxanthin.

It is a further object of the present invention to provide a carotenoid in isolated or purified or extracted or enriched form obtainable from or obtained by a microorganism capable of producing carotenoids with algae a high rate, preferably capable of producing astaxanthin with a high rate.

It is a further object of the present invention to provide a microorganism useful in the production of a carotenoid, preferably in the production astaxanthin, which is easily manageable, easily cultivable and from which the desired product can be obtained in high yields and economically.

It is an addition object of the present invention to provide products and goods containing a microorganism capable of producing carotenoids with a high rate, preferably capable of producing astaxanthin with a high rate.

It is an addition object of the present invention to provide products and goods containing a carotenoid or a carotenoid pigment in an isolated or purified or extracted or enriched form obtainable from or obtained by a microorganism capable of producing carotenoids with a high rate, preferably capable of producing astaxanthin with a high rate.

It is also an object of the present invention to provide the use of a microorganism capable of producing carotenoids economically and in high yields, preferably astaxanthin, for the manufacture of products and goods, especially for the production of animal feed, food, cosmetics or pharmaceuticals or additives thereto.

It is also a further object of the present invention to provide the use of a carotenoid, in particular astaxanthin, produced by a suitable microorganism for the manufacture of products and goods, especially for the production of animal feed, food, cosmetics or pharmaceuticals or additives thereto.

Furthermore it is an object of the present invention to provide the use of a carotenoid or a carotenoid pigment in an isolated or purified or extracted or enriched or immobilized form for the manufacture of products and goods, especially for the production of animal feed, food, cosmetics or pharmaceuticals or additives thereto, the carotenoid or carotenoid pigment is obtainable from or obtained by a microorganism capable of producing carotenoids with a high rate, preferably capable of producing astaxanthin with a high rate.

In addition it is an object of the present invention to provide a kit or a kit-of-parts comprising a carotenoid or a carotenoid pigment in isolated or purified or extracted or enriched or immobilized form or a suitable microorganism useful in the production of a carotenoid, preferably in the production astaxanthin, and/or products and goods containing a carotenoid, preferably astaxanthin, and/or a finished product or a manufactured article, which may or may not contain a carotenoid, preferably astaxanthin, which are contained or packaged spatially separated in one or more containers.

The biosynthesis as well as the production of carotenoids by different microorganisms is known in the art.

Examples of astaxanthin-producing microorganisms include the red yeast *Phaffia rhodozyma*, bacteria belonging to the Genera *Brevibacterium, Mycobacterium* and *Agrobacterium*, for example *Agrobacterium alcaligenes*, and the green alga *Haematococcus pluvialis*.

It is well known that in prokaryotes conserved enzyme catalysed reactions mediate the early reactions of carotenoid biosynthesis which seem to follow the same route in all prokaryotic and eukaryotic organisms.

The de novo biosynthesis of carotenoids is starting from isoprenoid precursors, commonly beginning with acetyl-CoA, which is then converted to mevalonic acid.

The specific part of the pathway begins with the condensation of two molecules of geranylgeranyl pyrophosphate to form phytoene, which is a colourless carotene, catalysed by prenyl transferases. A head-to-head condensation of two molecules of geranylgeranyl pyrophosphate leads to prephytoene pyrophosphate. In a subsequent two-step reaction the pyrophosphate moiety is removed and the colourless 15-cis-phytoene is formed.

Following four desaturation (also dehydrogenation) reactions 15-cis-phytoene is converted to lycopene. It should be noted that each of this membrane-bound dehydrogenation reactions increase the number of conjugated double bonds by two such that the number of conjugated double bonds increases from three in 15-cis-phytoene to eleven in lycopene, which is the pigment making the mature tomatoes red.

From cyanobacteria, algae and plants it is known that a single membrane-bound enzyme phytoene desaturase catalyse the first two desaturation reactions, from 15-cis-phytoene to ζ carotene. Since the ζ-carotene is mostly in the all-trans configuration, a cis-trans isomerization is presumed at this site in the pathway. Again, in cyanobacteria, algae and plants ζ-carotene in transformed to lycopene via neurosporene.

Two cyclisation reactions are catalysed by a single membrane-bound enzyme lycopene β-cyclase converting lycopene to β-carotene.

The known xanthophyll variants are formed by the addition of various oxygen-containing side groups, such as hydroxy-, methoxy-, oxo-, epoxy-, aldehyde or carboxylic acid moieties. However, in the end little is known about the formation of xanthophylls. What is known is that hydroxylation of β-carotene requires molecular oxygen in a mixed-function oxidase reaction. The oxygenation and hydroxylation reactions leading to astaxanthin are catalysed by β-carotene oxygenase or β-carotene hydroxylase, respectively.

The lipophilic pigment astaxanthin (3,3'-dihydroxy-β,β-carotene-4,4'-dione) was first described in aquatic crustaceans as an oxidized from of β-carotene. This pigment was later found to be very common in many marine animals and algae. However, only few animals can synthesize astaxanthin de novo from other carotenoids and most of them obtain it in their food. In the plant kingdom, astaxanthin occurs mainly in some species of cyanobacteria, algae and lichens.

RELATED ART

If one is confronted with the problem to provide a nature born carotenoid, preferably astaxanthin, with high yield and under effective economical conditions, it is a conditio sine qua non that three requirements are fulfilled: the method for producing the desired compound must be uncomplicated and not laborious, the source must be an organism or a cell capable of synthesizing the carotenoid which is easily cultivable and showing an optimal cell growth rate, the organisms must produce the carotenoid within a short period of time and with a maximum rate of yield.

It is known from the international patent application WO92/22648 to produce astaxanthin in the yeast *Phaffia rhodozyma* by culturing this microorganism in shake flasks to the stationary phase, treating the cells with different mutagens and culturing the cells in the presence of a inhibitor of phytoene dehydrogenase.

The European patent application EP 1229126 A1 relates to a process for producing different carotenoid pigments by controlling the concentration of dissolved oxygen in a culture during cultivation of a certain bacterial strains.

The international patent application WO 01/62894 discloses a process for production of carotenoids by using of a microorganism belonging to the Order Thraustochytriales, which are unicellular saprophytes and which are cultured under heterotrophic growth conditions till the steady state growth phase and beyond it.

The application WO 91/18108 relates to a method for the fermentation of the heterotrophic alga *Neospongiococcum extentricum* and to the production of xanthophyll therefrom by continuously diluting the fermentation broth with fresh fermentation medium From what is described supra under the headings background of the invention and prior art it is thus a widely recognized need for, and it would be highly advantageous to have, carotenoids, preferably astaxanthin, producing microorganisms. In particular, it would be desirable to develop methods for production of a carotenoid, preferably astaxanthin, by fermentation or cultivation of a suitable alga capable of producing high levels of said carotenoids within a short period of time.

Other features of the present invention, which are of advantage, will become apparent from the following detailed description of the invention and the claims.

BRIEF SUMMARY OF THE INVENTION

The problem underlying the present invention is to provide microorganisms belonging to the photoautotrophic algae of the Class Chlorophyceae, which are capable of producing carotenoid or carotenoid containing material, preferably astaxanthin or astaxanthin containing material, obtainable within a shorter period of time, with less business expenditure, with less amount of work, without considerable loss of viability of the biological material and more efficiently than what has been obtained in the prior art.

In particular the present invention make use of microorganisms belonging to the photoautotrophic algae of the Order Volvocales, preferably belonging to the Family Haematococcaceae, more preferably to the Genus *Haematococcus*, most preferably to the species *Haematococcus pluvialis*.

More specifically, the task of present invention is to solve the problem of low productivity of carotenoids, preferably of astaxanthin, of cultures of microorganisms belonging to the photoautotrophic algae of the Order Volvocales, preferably belonging to the Family Haematococcaceae, more preferably to the Genus *Haematococcus*, preferably cultures of *Haematococcus pluvialis*, by obtaining mutants thereof exhibiting a higher content in the said pigment and early accumulation of it and keeping growth rate substantially constant in comparison with the corresponding wild type microorganism (i.e. is substantially the same as in the wild strain). The invention thus provides methods, which increase the productivity of the cultures according to the invention, making cultures of the said microorganisms, preferably cultures of *Haematococcus pluvialis*, profitable.

In particular, methods are described for obtaining carotenoid, preferably astaxanthin, super-producing and early accumulation mutants, the methods involve classical mutagenesis of photoautotrophic algae of the Genus *Haematococcus*, preferably of the species *Haematococcus pluvialis*, by a mutagen, for example N-methyl-N'-nitro-nitrosoguanidine, and consecutive selection strategy based on resistance to an agent that inhibit the carotenoid biosynthesis in at least one step of the pathway, preferably to herbicides, for example norflurazon, diphenylamine and nicotine.

Accordingly, the present invention relates to a method for producing and providing a carotenoid or a carotenoid pigment, respectively, preferably astaxanthin, by culturing a mutant microorganism resulting in a high yield of the said carotenoid, an early accumulation of the said carotenoid, a short time of induction of carotenogenesis and a growth rate substantially similar to the corresponding wild type material.

The method also comprises suitable microorganisms belonging to photoautotrophic algae from the Class Chorophyceae, in particular from the Family Haematococcaceae, most particular from the Genus *Haematococcus*, preferably the species *Haematococcus pluvialis*, capable of producing an effective amount of the carotenoid pigment and culturing the said microorganism under conditions appropriate for effective production of the carotenoid pigment and recovering same.

The present invention further provides mutant strains of the said microorganisms which super-accumulates carotenoids or carotenoid pigments in very high yields and within a short period of time, exhibiting a growth rate substantially similar when compared with the corresponding wild type strains, which also means that the growth rate of the mutants is preferably keeping constant.

In addition, preferred culture conditions are given as well as preferred conditions for mutagenesis and for the selection of the mutants are described.

The present invention also relates to products and goods, comprising food and animal feed, cosmetic and pharmaceutical preparations comprising a carotenoid pigment or compound or a suitable microorganism according to the invention including parts thereof and mixtures of the said microorganism with carrier material.

As used herein the term "effective amount" or "effective production" means an amount or a production rate that is sufficient to recover carotenoid pigment form the appropriate wild type on the basis of visual means or inspection.

As used herein the term "recovering" or "recover" refers to a process or means that is suitable to obtain carotenoid or carotenoid containing material comprising technologies such as isolation, extraction from the medium or from the microorganism as a whole or from parts thereof, or from cells or cells debris or parts thereof, cell disruption by any chemical, enzymatic or mechanical method and devices, centrifugation, homogenisation of the cells of the microorganism or of the microorganism as a whole.

As used herein the term "carotenoid" stands for the chemical compound as such as well as for a pigment of the appropriate dye, if not otherwise stated. For example, in case of astaxanthin the chemical compound 3,3'-dihydroxy-$\beta,\beta$-carotene-4,4'-dione in form of the (3S,3' S)-isomer is meant as well as the dye as a pigment.

From time to time the nomenclature or the taxonomical classification of living organisms, in particular that of microorganisms, is revised so that the scientific names used herein may not necessarily given the name that is currently valid. For example it seems that the yeast *Phaffia rhodozyma* is renamed now bearing the name *Xantophyllomyces dendrorhous*. In addition, it seems that the taxonomical system of the algae is currently also under revision so that, for instance, the Family Haematococcaceae is obviously replaced by the name Chlamydomonadaceae to which the Genus *Haematococcus* belong to. Therefore, a person skilled in the art can unambiguously identify the microorganisms mentioned in this application, irrespective of their current taxonomic naming or classification.

As used herein the term "capable of producing" means that the said producer in fact produces or provides the said product, in the present case a carotenoid or astaxanthin, if not otherwise stated.

As used herein the term "volumetric productivity" (Vp) refers to a calculation based on the formula $$Vp = \frac{(\text{biomass})(\text{carotenoid})(0.72)}{\text{reaction time }[h]}$$

wherein biomass is defined as grams per liter, carotenoid as mg per grams of cells and the number 0.72 e factor relating carotenoid assay values to external xanthophyll values according a convention by the Association of Official Analytical Chemists.

As used herein the term "room temperature" refers to a temperature between 20 and 25° C. It should be understood that this also means that the temperature is not critical for an experiment as long as it is carried out within the range of temperature given above. If in turn one experiment is carried out at 21° C. and another one at 23° C. both experiments are carried out within the definition "room temperature". In laboratory manuals and for numerical convenience 20° C. or 21° C. are often used.

DETAILED DESCRIPTION OF PREFERRED EMBODIMENTS

The present invention pertains to an improved method for producing a carotenoid with high yield, process for generating carotenoid-producing microorganisms or cells and microorganisms obtained by the method and some uses for the said carotenoids.

It has now surprisingly been found that the problem according to the state of the art and underlying the present invention, in particular to produce a carotenoid in high yields and most efficiently with respect to productivity and manageability, comprising growth rate, expenditure, time, labour, costs, safety, isomerism, can be solved by a method by using a microorganism belonging to the photoautotrophic algae of the Class Chlorophyceae capable of producing an effective amount of a carotenoid comprising the steps (a) culturing the microorganism under photoautotrophic conditions in a liquid medium,
(b) harvesting the microorganism within the exponential growth phase,
(c) mutagenizing the microorganism,
(d) selecting the mutants based on the resistance of cells of the microorganism to an agent that inhibit the carotenoid biosynthesis in at least one step of the pathway,
(e) recovering or isolating a mutant capable of producing a carotenoid with a volumetric yield of at least 5.0 mg$l^{-1}$, preferably of at least 7.0 mg$^{-1}$, most preferably of at least 8.0 mg$^{-1}$ after three days of induction of the red phase (carotenogenesis) or within a period of time substantially not exceeding three days of induction of the red phase,
(f) recovering or isolating the carotenoid from the medium where carotenogenesis was induced, and/or from the mutant microorganism or parts thereof, by extraction and/or by centrifugation and/or by disrupting isolated cells of the mutant microorganism or parts thereof by chemical, enzymatic and/or physical treatment and/or by homogenization of the mutant cells and/or the mutant microorganism or parts thereof, or from cell debris and/or by lyophilisation of the mutant microorganism or parts thereof.

The following protocol is indented only to give a rough survey of the procedure underlying the present invention.
1. Grow the algae cells in an inorganic medium till the exponential phase, preferably the mid-exponential phase,
2. Mutagenize the cells with a useful mutagen or noxa to obtain a suitable viability,
3. Incubate the cells in liquid medium during a sufficient time to allow the recovering of the cells and/or the new phenotype expression,
4. Spread the cells on agar medium containing an agent that inhibit the carotenoid biosynthesis in at least one step of the pathway and incubate the cells preferably under light at a suitable temperature,
5. Subculture resistant colonies on new agar medium containing the agent that inhibit the carotenoid biosynthesis in at least one step of the pathway, to purify mutants and/or to check their resistance,
6. Analyze growth and carotenoid content of mutants resistant to the agent that inhibit the carotenoid biosynthesis in at least one step of the pathway spectophotometrically after growing them in a suitable culture, preferably in a still culture,
7. Analyze the promising mutants by suitable methods of analysis, which could be used for a second or further round of mutagenesis.

More precisely, the method of the present invention is based on the finding that if a microorganism belonging to the photoautotrophic green algae of the Class Chlorophyceae is cultured in a liquid medium it is possible to select microorganisms under suitable conditions, particularly under photoautotrophic conditions, which exhibit a high level of the desired carotenoid when harvested in the course of the exponential growth phase following incubation with at least one mutagen.

As regards the microorganism belonging to the photoautotrophic green algae of the Class Chlorophyceae it is preferred to use those, which belong to the Order Volvocales, preferably to the Family Haematococcaceae, more preferably to the Genus *Haematococcus*. The most preferred microorganism according to the present invention is the species *Haematococcus pluvialis* from which the strains CCAP 34/8 and SAG 34-1b are used exemplarily in the present invention. The strains CCAP 34/8 and SAG 34-1b can be obtain from CCAP Culture Collection and from SAG Culture Collection and are commercially available.

One important factor that contributes to the determination of a commercially effective level of carotenoid production are the costs of the production process, including culturing the microorganism and modifying it so as to obtain a high rate of productivity of the desired carotenoid.

It has been found that the microorganisms may easily be cultured inexpensively in a common mineral salt medium. There is no necessity that the mineral salt medium contains a carbon source. Accordingly, the mineral salt medium is preferably an inorganic medium that substantially, more preferably completely, does not contain a carbon source or any other organic material or nutrients. In general, the microorganism is cultured in a mineral medium preferably not exhibiting high-saline culture conditions.

The mineral medium may be composed by salts or minerals commonly used in culturing said photoautotrophic algae. Thus, the elements of the mineral medium may be selected from the group consisting of Na, Ca, K, Mg, B, Mn, Zn, Co, Mo, or Cu.

In particular, the culture medium is an aqueous solution comprising $NaNO_3$, $Ca(NO_3)_2 \cdot 4H_2O$, $KH_2PO_4$, $MgSO_4 \cdot 7H_2O$, $H_3BO_3$, $CaCl_2$, EDTA-FeNa, EDTA-$Na_2$, $MnCl_2$, $ZnCl_2$, $CoCl_2$, $(NH_4)_6Mo_7O_{24}$, $CuSO_4$. Preferably, at least one vitamin or a vitamin solution can be added to the mineral medium, preferably in form of a sterilized aqueous solution.

As an example the mineral medium may contain per liter 1.0 g NaNO$_3$; 0.04 g Ca(NO$_3$)$_2$.4H$_2$0; 0.05 g KH$_2$PO$_4$; 0.049 g MgSO$_4$.7H$_2$0; 0.01 g H$_3$B0$_3$; 10 mg CaCl$_2$, 4.5 mg EDTA-FeNa, 4.5 mg EDTA-Na$_2$, 2.8 mg MnCl$_2$.4H$_2$0; 0.042 mg ZnCl$_2$; 0.04 mg CoCl$_2$.6H$_2$0; 0.018 mg (NH$_4$)$_6$Mo$_7$O$_{24}$; 0.04 mg CuSO$_4$.5H$_2$0; 100 ml of a vitamin solution. The vitamin solution may contain any useful water soluble vitamins from which it is known that they are of advantageous in culturing the photoautotrophic green algae according to the invention. In particular, the vitamin solution may contain biotin, thiamine (B$_1$) or cobalamine (B$_{12}$), for example (per liter) 0.2 g biotin, 1.0 g B$_1$ and 0.05 g B$_{12}$. Preferably the vitamin solution is sterilized separately by filtration.

Preferably, the vitamin solution is added to the medium before inoculation of the microorganism into the medium is carried out.

Accordingly, the microorganisms of the present invention are cultured in a mineral medium as described supra under photoautotrophic conditions appropriate for effective production of the desired carotenoid.

Preferably, the culture conditions comprise the still cultures (Erlenmeyer flask) in liquid mineral medium as mentioned above under continuous white light at 70 µE m$^{-2}$s$^{-1}$ in the green phase and at 180 µE m$^{-2}$s$^{-1}$ in the red phase, at 25° C.

There are several methods in the art to harvest microorganisms or cells belonging to the photoautotrophic algae. For example, cells of the microorganism can be harvested by centrifugation or filtration or even by sedimentation and consequent decantation of liquid phase. The cells can preferably be harvested by centrifugation at 3000 rpm during 3 min.

Once the cells are harvested one or more subsequent washing steps can be necessary in order to remove undesired products or other parts or particles from the cells.

Since one aspect of the present invention involves the generation of a microorganism that is capable of synthesizing a carotenoid in high yields and most efficiently with respect to productivity and manageability it is necessary to alter or manipulate the wild type microorganisms in such a way that the productivity of the altered or manipulated microorganism is superior of the former one without substantial loss of growth rate.

Such alterations or manipulations can be carried out by various methods. The microorganism can be treated with at least one mutation inducing agent or noxa, hereinafter referred to as artificial induced mutation or mutagenesis. Alternatively, there is also the possibility to take advantage of the occurring of spontaneous mutations.

However, mutagenizing the microorganisms by using suitable agents or noxa are preferred.

In case of artificial mutagenesis there are several options known in the art. Mutations can be induced on the basis of chemical or physical mutagens as well as on the basis of biological active substances.

Among the chemical, physical and biological mutagens several useful compounds are known in the art from which the following are particular useful.

For instance such mutagens or noxa are of particular interest which are selected from the group consisting of intercalating agents, alkylating agents, deaminating agents, base analogs, electromagnetic radiation comprising radioactive radiation, γ-rays and x-rays, ionizing radiation, ultraviolet-light or elevated temperature, biological active substances comprising transposons including known technologies connected therewith comprising gene recombinant technologies, transposon mutagenesis and the like. However, mutations based on a spontaneous mutation are also included in this context.

In particular, among the intercalating agents the acridine derivatives or the phenanthridine derivatives such as ethidium bromide also known as 2,7-diamino-10-ethyl-6-phenylphenanthridium bromide or 3,8-diamino-5-ethyl-6-phenylphenantridinium bromide are well known.

As to the alkylating agents compounds such as nitrosoguanidine derivatives or ethyl methanesulfonate; ethyl ethanesulfonate, nitrous acid, or HNO$_2$ are also useful. However, regarding the nitrosoguanidine derivatives the compound N-methyl-N'-nitro-nitrosoguanidine is of particular interest in order to carry out the present invention.

Concerning the base analogs the compound 5-bromo-uracil, which is also known as deoxynucleosid 5-bromodeoxyuridine, or 2-aminopurine can be used.

Among the transposons there are a lot of methods published in the literature that describes transposon mutagenesis. For example, retrotransposons or DNS transposons, for example Mu phage transposon, or transposon-tagging, are well known and are available for the induction of mutations. In addition, site-directed mutagenesis can also be achieved by using known technologies such as linker-insertion mutagenesis, generation of deletion mutants or oligonucleotide-directed mutagenesis. In general, all known biological methods based on gene recombination are included within the context of the above methods. Because the skilled person is aware of the great variety of the adequate literature there is no need to cite specific ones.

The microorganisms to be mutagenized can be exposed to the mutagen or the mutation inducing agents or noxa according to any known methods. However, according to the present invention, it is preferred that artificial mutagenesis is performed with at least one chemical mutagen, in particular with an alkylating compound, more particular with a nitroso-compound, especially with a nitrosoguanidine derivative. Among the nitrosoguanidine derivatives the compound N-methyl-N'-nitro-nitrosoguanidine is preferred.

In general mutagenesis can be carried out by exposing a suitable quantity of cells of the photoautotrophic algae to be mutagenized to a mutagen or mutagen-inducing agent within an appropriate time and conditions.

In particular, mutagenesis can be performed by suspending cells to be mutagenized in a sterilized liquid medium or in sterilized water in an amount between 10$^7$ to 10$^9$ cells, for example exhibiting a density of about 10$^8$ cells, or by spreading them on an agar plate and exposing them to the mutagen. In case of a liquid medium in which the cells are suspended it has been found that an alkylating agent, in particular a nitrosoguanidine derivative, preferably N-methyl-N'-nitro-nitrosoguanidine (NG) is effective for producing mutants, which are of particular value for the purpose of the present invention.

Mutagenesis can be performed in a liquid medium as mentioned above in suitable flasks of a volume between 5000 ml and 10 ml or between 1000 ml and 100 ml between 0° C. and 40° C., in particular between 5° C. and 30° C., preferably at a temperature between 20° and 25° C., that means at room temperature.

In case of a physical mutagen such as x-ray or UV-light culturing on an agar plate is preferred.

The time of exposition of the cells to the mutagen depends on the nature of the mutagen to be used. In particular, if a chemical mutagen is used, such as a nitrosoguanidine derivatives, for example N-methyl-N'-nitro-nitrosoguanidine (NG), the time of contacting the cells with the mutagen is between 1 minute and 24 hours, preferably between 30 minutes and 6 hours, more preferably between 1.0 and 3.0 hours, for example one hour. The concentration of the chemical mutagen may easily be chosen on the basis of the viability of the cells to the mutagen. In case of a chemical mutagen such as an alkylating agent as mentioned above, for example N-methyl-N'-nitro-nitrosoguanidine, it can be advisable to conduct a series of simple tests in order to determine the viability rate of the cells to be mutagenized.

On the basis of the results obtained through such experiments it could be shown that a viability rate of the cells between 1 and 80%, particular between 2 and 50%, preferably in the range of 5 to 10% and 50% is suitable for the purpose of the present invention. In the case of NG a concentration between 10 mg $l^{-1}$/or 0.07 mM and 1000 mg $l^{-1}$/or 6.80 mM, in particular between 20 mg $l^{-1}$/or 0.14 mM and 500 mg $l^{-1}$/or 3.40 mM, most particular between 50 mg $l^{-1}$/or 0.34 mM and 400 mg $l^{-1}$/or 2.38 mM, preferably in a concentration of 200 mg $l^{-1}$/or 1.36 mM and 350 mg $l^{-1}$/or 2.38 mM was found to be particular useful.

In case of mutagenesis using the microorganism *Haematococcus pluvialis* strain CCAP 34/8 and strain SAG 34-1b, which are described in the examples in detail, it has been found that NG in concentrations resulting in 5 to 10% or 50% of viability, respectively, were particular useful. These concentrations corresponds to 200 mg $l^{-1}$/or 1.36 mM (for *H. pluvialis* CCAP 34/8 strain and 5 to 10% of viability, for example) or 50 mg $l^{-1}$/or 0.34 mM (for *H. pluvialis* CCAP 34/8 strain and 50% of viability, for example) and to 350 mg $l^{-1}$/or 2.38 mM (for *H. pluvialis* SAG 34-1b strain and 5 to 10% of viability, for example) or 150 mg $l^{-1}$/or 1.02 mM (for *H. pluvialis* SAG 34-1b strain and 50% of viability, for example), respectively, of NG.

After treatment with the mutagen, in particular with a chemical mutagen, it is of advantage to wash the cells at least once with sterile water following incubation in liquid mineral medium. Preferably, the cells are washed twice with sterile water and then incubated in a liquid medium as described supra during 6 to 72 hours, particular during 10 to 48, preferably during 24 hours.

This would allow the cells to recover from damages caused by the mutagen and/or new phenotype expression.

The selection of mutants is in particular based on the resistance of mutated cells to at least one agent that is capable of inhibiting the carotenoid biosynthesis in at least one step of the pathway. It has been found that it is of advantage if the inhibiting agents are involved in affecting at least one of the enzymes that catalyse the first two desaturation reactions from 15-cis-phytoene to ζ-carotene, which is the phytoene desaturase, or that catalyse the two cyclisation reactions converting lycopene to β-carotene, which is the lycopene β-cyclase, or that catalyse the oxidation and hydroxylation leading from β-carotene to astaxanthin, which is the β-carotene oxygenase or the β-carotene hydroxylase, respectively. Therefore, the use of at least one of an agent that is capable of inhibiting at least one of these enzymes is preferred for realising the present invention. Accordingly, it is preferred to perform the selection of mutants on a agar medium, particular comprising a composition of a mineral medium as described above, containing at least one agent that is capable of inhibiting the carotenoid biosynthesis in at least one step of the pathway, preferably, under light conditions such like continuous white light of (70-100) $\mu E\ m^{-2}s^{-1}$, till to appearance of colonies, what depends on the mutagenized organism. For example, in case of *H. pluvialis* it takes 3-5 weeks.

However, the use of a combination of at least two of these enzyme inhibiting agents are particular preferred. It is therefore a preferred method of the present invention if the agent is an inhibitor of an enzyme selected from the group consisting of phytoene desaturase, lycopene β-cyclase, β-carotene oxygenase and β-carotene hydroxylase, or a mixture thereof. The combination comprises agents, which are capable of inhibiting all of these said enzymes, is optimal for carrying out the invention. It has further been found that if the enzyme inhibiting agent is a herbicide, preferably a herbicide selected from the group consisting of norflurazon, diphenylamine and nicotine, or a mixture thereof, selection of the mutants can be performed with particular efficiency.

From norflurazon it is known that this herbicide abort the biosynthesis of astaxanthin at the beginning of the pathway inhibiting phytoene desaturase. Nicotine is a specific inhibitor of the lycopene β-cyclase and, thus, does not allow the conversion of lycopene to β-carotene. The herbicide diphenylamine inhibits the enzymes β-carotene oxygenase and in less extent β-carotenehydroxylase and at higher concentrations (above 100 μM) also the phytoene desaturase.

The screening of the mutants is based on the use of media containing at least one of these enzyme inhibiting agents, preferably a combination or mixture of the three agents as specified above. Accordingly, when wild type cells of the microorganism according to the present invention are spread on agar media containing the said enzyme inhibiting agents, preferably herbicides, they are blocked in the corresponding enzymes and cannot perform the biosynthesis of the carotenoid, especially of astaxanthin.

The agar medium used for these purposes is composed as known in the art. In general, all known agar based media can be used. For instance a medium containing a concentration of agar between 1.0 and 2.0%, preferably of 1.5%, is usually suitable for this purpose.

The optimal concentration of the enzyme inhibiting agent to be used for selection depends mainly on the nature of the compound and of the organism to be treated. It is therefore recommended to determine the minimal concentration of the appropriate enzyme inhibiting agent from which it is expected that it inhibit the growth of the cells of the wild type microorganism.

These concentrations should advantageously be applied for the selection of the mutants.

It has been found that, for example, norflurazon can be applied with a concentration between 0.01 and 100 μM, in particular between 0.1 and 50 μM, more particularly between 0.5 and 10 μM, preferably between 1.0 and 5 μM.

As regards diphenylamine an amount in the range from 0.1 μM to 3.0 mM, in particular from 1.0 μM to 2.0 mM, more particularly from 10 μM to 1.0 mM, preferably from 50 μM to 500 μM is suitable.

The concentration of nicotine can be chosen from the range of 0.1 μM and 5.0 mM, in particular from 1.0 μM to 3.0 mM, more particular from 10 μM to 2.0 mM, preferably from 100 μM to 1.0 mM.

It is of advantage if the incubation of the cells is performed at light. This means a light intensity between 10 $\mu E\ m^{-2}s^{-1}$ (white light) and 500 $\mu E\ m^{-2}s^{-1}$, particularly between 20 $\mu E\ m^{-2}s^{-1}$ and 200 $\mu E\ m^{-2}s^{-1}$, preferably 70-100 $\mu E\ m^{-2}s^{-1}$.

The incubation is conducted between a temperature range of 0° C. and 40° C., particularly in the range of 10° C. and 35° C., most particularly between 20° C. and 30° C., preferably at 25° C.

If these cells grow under light conditions they die, since in the absence of astaxanthin the cells do not have protection from photo-oxidative stress caused by a block in their carotenoid biosynthesis. Therefore, the selection is advantageously performed under light condition. The light conditions comprise 70-100 µE m$^{-2}$s$^{-1}$ of white light (fluorescent lamps) during all selection period of time till resistant colonies appearance.

The light intensity can be chosen in the range of 10 to 200 µEm$^{-2}$s$^{-1}$, for example 70 µEm$^{-2}$s$^{-1}$.

The mutagenized cells which overexpress the corresponding enzyme may have some amount of the enzyme free from inhibitors and can follow carotenogenesis to the end product. Such mutants will survive on enzyme inhibiting agents containing medium, in particular herbicide containing medium, under light conditions (see above), but unfortunately, not all the cells in a mutagenized culture which grow on selective medium are resistant to at least one of these enzyme inhibiting agents due to a higher expression of corresponding carotenogenic enzyme. The mutants with enhanced level of astaxanthin production can be distinguished from other type of mutants particularly only after analysis of their liquid cultures which may include extraction and spectrophotometric or High Performance Liquid Chromatography (HPLC) measurement of carotenoids.

Resistant colonies from which it is expected to be good candidates can be subcultured at least twice on new agar medium containing an inhibitor of at least one enzyme of the pathway, particularly an herbicide, as described supra, in order to purify them and to check their resistance.

Most surprisingly it has been found that according to the present invention mutants can be identified, recovered and isolated that not only provide high yields of carotenoid, in particular astaxanthin, within an unexpected short period of time, low costs and under economical conditions, but also exhibit similar growth (dry weight) to the corresponding wild type microorganism, which is also of high importance for industrial use.

The purified mutants, which are resistant to at least one agent that inhibit the carotenoid biosynthesis in at least one step of the pathway were grown in cultures, in particular small cultures having preferably a volume between 5 and 100 ml and then growth and astaxanthin content were analysed spectophotometrically.

The content in astaxanthin of the most promising mutants were analysed by HPLC. In order to analyse many mutants and to evaluate the carotenoid production, in particular the astaxanthin production, by the mutants and by the corresponding wild type microorganism, both types of cells are separately grown in liquid mineral medium as described above. For this purpose it is of certain advantage that the mutants as well as the wild type cells are cultured in still cultures, preferably in small still cultures, that is without shaking, having a volume of 5 ml to 100 ml, preferably from 10 ml to 50 ml, for example 20 ml.

The purified mutant's colonies keeping resistance to the corresponding agent that inhibit the carotenoid biosynthesis in at least one step of the pathway can then be checked on growth rate in microtiter plates. For instance, this can be done by using Microtiter Plates Rider (The Microtiter plates are commercial available and allow to follow the growth of till to 96 cultures at the same time).

Advantageously, only the well growing resistant colonies should be chosen for the analysis as to the astaxanthin accumulation in their cells. The analysis can best be performed in liquid mineral medium in still cultures as mentioned above starting with a cell density in the range of approximately 10$^4$ and 10$^5$ cells/ml for both mutants and wild type cells. For this purpose an inoculum was obtained from agar cultures and was grown in still or preferably in aerated cultures (because growth is faster) in inorganic medium at 70 µEm$^{-2}$s$^{-1}$ during some days.

The subsequent culturing of the cells can be carried out within a temperature range of 0° C. and 40° C., particularly 5° C. and 35° C., more particularly 10° C. and 30° C., preferably at 25° C.

The initial occurring green phase of the culture is grown under light, for example by using a fluorescent lamp with a wavelength λ in the range of 400 to 700 nm and an intensity in the range of 20 to 200 µEm$^{-2}$s$^{-1}$, preferably in the range of 70 to 100 µEm$^{-2}$s$^{-1}$. However, it has been found that the irradiance should not exceed 100 µEm$^{-2}$s$^{-1}$.

For the subsequent induction of the red phase it is of advantage to remove the medium from the culture of the green phase and to replace it by the same volume of approximately 20 ml of sterilized distilled water. This culture is generally illuminated at a higher irradiance than the green phase culture. In order to remove the medium of the green phase culture various separation technologies may be used, for instance centrifugation or filtration or sedimentation, from which centrifugation is preferred. In this case centrifugation can be performed by using a rotation resulting in a range of 5000×g and 500×g, particularly 3000×g and 1000×g preferably 1800×g and 1300×g. For example, with a centrifuge such as Megafage 1.0 of Heraeus and using a rotor type such as B 2205 good results can be obtained.

As mentioned above the cells of the red phase were generally illuminated at a higher irradiance to the green phase culture. It has been found that very good results can be achieved with irradiation above 70 µEm$^{-2}$s$^{-1}$, particularly in the range of 80 and 500 µEm$^{-2}$s$^{-1}$, more particularly between 100 and 300 µm$^{-2}$s$^{-1}$, preferably between 100 and 250 µEm$^{-2}$s$^{-1}$. The illumination procedure can be carried out using conventional light sources as commonly used in these cases, such as white light of fluorescent lamps.

For further analysis of the mutant cells as to their carotenoid content spectrophotometric analysis or analysis by HPLC can be performed.

The spectrophotometric analysis can be carried out using known technologies. In particular extracted and resuspended in acetone carotenoids can be measured at 480 nm on spectrophotometer Beckman BU 650. The amount of astaxanthin was calculated using an extinction coefficient of 2100 for 1% astaxanthin solution.

For this purpose it may be of advantage to disrupt the cells before analysis starts, for instance, by enzymatic, chemical, or physical measurements including lysis, sonification, shearing, pressing of the cells or the like.

The recovery or isolation of the carotenoid for further use or analysis can also carried out by known extraction procedures, according to which cells of the microorganism are exposed to solvents or enzymes, for example cell wall lysing enzymes. In particular, the cells may be harvested by centrifugation, for example at 1900×g for 3 minutes, and washed once or twice in water. The cell pellet that is obtained by centrifugation is broken with mortar and pestle with the aid of aluminium powder and then resuspended in a suitable organic solvent, for instance in acetone or methanol and the carotenoid extract is separated from the cell debris by centrifugation at 1900×g, saponificated with a mixture of the same volumes of 2% (w/v) solution of KOH in methanol and diethyl ether, then the supernatant is evaporated under N$_2$ and the pellet is resuspended in acetone, centrifuged and analyzed by HPLC. The process is carried out at a temperature between 0° C. and 40° C., particularly 5° C. and 35° C., more particularly 10° C. and 30° C., preferably at room temperature, preferably in the dark and the carotenoid extract is kept at a temperature between −20° C. and 25° C., more particularly −20 and 4° C., preferably at −20° C. Optionally, the samples obtained can be collected and centrifuged once more to separate undesired particles from the cells or extracts. The supernatant can be used for further spectrophotometric analysis, as mentioned above, for HPLC or other technologies concerning analysis of carotenoids or cells containing same, such as thin layer chromatography, for example using Kiesel gel plates, gas chromatography or magnetic resonance chromatography.

In general, the carotenoid according to the present invention can be isolated by methods known in the art. For example the carotenoids can be isolated by extraction from the microorganism or parts therefrom, such as cell debris or physically pressed cells, using an organic solvent as mentioned above.

As regards analysis by HPLC reverse phase HPLC can be used according to known procedures. In particular, a Waters Spherisorb S5 ODS18 4.6×250 mm cartridge column can be used and a solvent linear gradient from 100% solvent A (acetonitrile:methanol: 0.1 M Tris-HCl, pH 8.0 [84:2:14]) to 100% solvent B (methanol:ethyl acetate [68:32]) for 15 min, followed by 3 min of solvent B, which is pumped by using a Dual Dispensity system with a flow rate of 1.2 ml min$^{-1}$ from which carotenoid pigments can be eluted. The pigments can be detected by using a photodiode-array detector (Waters 2996) at 440 nm. The concentration of individual carotenoids are determined using standard curves of purified pigments at known concentrations.

Astaxanthin was determined also by measuring the absorbance at 477 nm using an extinction coefficient of 2100.

It is known from the literature, that the obtained carotenoid astaxanthin is achievable in the pure form of the (3S,3'S) isomer.

The present invention also comprises a method of generating carotenoid-producing, in particular astaxanthin-producing, microorganisms belonging to photoautotrophic algae of the Class Chlorophyceae having a carotenoid dry weight content in the range of 10.0 mg (g dw$^{-1}$) to 20.0 mg, preferably between 11.0 and 17.0 more preferable between 12.0 and 16.0 most preferably between 13.0 and 15.0 mg (g dw$^{-1}$) or a volumetric yield of at least 5.0 mg 1$^{-1}$ mg after three days of induction of the red phase (carotenogenesis) or within a period of time substantially not exceeding three days of induction of the red phase comprising the steps (a) culturing the microorganism in a mineral medium to the exponential growth phase, preferably at mid exponential phase corresponding to a cell density in the range of an OD 0.1 and 0.3, preferably in the range of an OD 0.2, measured photometrically at a wavelength of 414 nm using a Labsystem iEMS Reader MF, (b) treating the microorganism with at least one mutation inducing agent or noxa, that inhibit the carotenoid biosynthesis in at least one step of the pathway, preferably affecting the enzymes phytoene desaturase, lycopene β-cyclase, β-carotene oxygenase and/or β-carotene hydroxylase, most preferably norflurazon, diphenylamine and/or nicotine.

(c) selecting the microorganism exhibiting a reduced growing in the presence of an agent, in particular a herbicide, that inhibit the carotenoid biosynthesis in at least one step of the pathway, preferably under light conditions, most preferably under continuous white light of fluorescent lamps (400-700 nm) of 100 µEm$^{-2}$s$^{-1}$ during 3-5 weeks and (d) optionally, isolating and purifying the microorganism from the culture medium.

As already mentioned above the agent in step (c) is preferably selected from the group consisting of an inhibitor of phytoene desaturase, an inhibitor of the lycopene β-cyclase, an inhibitor of β-carotene oxygenase and β-carotene hydroxylase. However, the agent is more preferably selected from the group consisting of norflurazon, diphenylamine and nicotine.

Regarding the carotenoid-producing photoautotrophic algae it is also preferred that this microorganism belongs to the Order Volvocales, particular to the Family Haematococcaceae, more particular to the Genus *Haematococcus*, most particular to the species *Haematococcus pluvialis*

It is also an object of the present invention to provide an established mutant strain capable of producing carotenoids in an enhanced level relative to the corresponding wild type microorganism. Such a mutant can be provided by a method, which comprises (a) cultivating a wild type microorganism belongs to the group of the photoautotrophic algae of the Class Chlorophyceae capable to produce carotenoids in a mineral salt medium, (b) harvesting the cells in the exponential growth phase, preferably at mid exponential phase corresponding to a cell density in the range of an OD 0.1 and 0.3, preferably in the range of an OD 0.2, measured photometrically at a wavelength of 414 nm using a Labsystem iEMS Reader MF.

(c) treating the microorganism with at least one mutagen, (d) exposing the cells to an agent, in particular a herbicide, that inhibits the carotenoid biosynthesis in at least one step of the pathway, and (e) selecting cells capable of producing carotenoids in a level higher than the wild type microorganism with a volumetric yield after three days of induction of the red phase (carotenogenesis) of at least 5.0 mg l$^{-1}$, preferably of at least 7.0 mg$^{-1}$, most preferably of at least 8.0 mg$^{-1}$ and which exhibit similar growth to the corresponding wild type microorganism.

In accordance with the disclosure as set forth above wild type microorganism in step (a) particularly belongs to the Order Volvocales, preferably to the Family Haematococcaceae, more preferably to the Genus *Haematococcus*, most preferably to the species *Haematococcus pluvialis*.

It is a preferred object of the present invention that the mutant is capable of producing a carotenoid according to step (e) within a period of time of not more than three days of induction of carotenogenesis.

A further preferred object of the present invention is that the mutagen used in step (c) of the method mentioned above is an agent or noxa, that inhibit the carotenoid biosynthesis in at least one step of the pathway, more preferably affecting the enzymes phytoene desaturase, lycopene β-cyclase, β-carotene oxygenase and/or β-carotene hydroxylase, most preferably norflurazon, diphenylamine and/or nicotine.

The present invention also discloses carotenoid-producing mutant microorganisms or strains, in particular astaxanthin-producing mutant microorganisms, with an initial carotenoid content of less than 5.0 mg 1$^{-1}$, exhibiting a carotenoid content of more than 5.0 mg 1$^{-1}$, preferably 7.5 mg 1$^{-1}$, when cultured in a liquid mineral medium, generated by the methods as described above.

In particular and as it will be described in detail in the examples preferred mutant microorganisms according to the present invention comprises those selected from the group consisting of strain MS13 deposited with Culture Collection of Algae and Protozoa (Dunstaffnage Marine Laboratory, Dunbeg, OBAN, Argyll PA37 1QA, Scotland, United Kingdom) on Dec. 14, 2006, under the accession No. CCAP 34/15, strain MC35 deposited with Culture Collection of Algae and Protozoa on Dec. 14, 20006, under the accession No. CCAP 34/16 and strain MC36 deposited with Culture Collection of Algae and Protozoa on Dec. 14, 20006, under the accession No. CCAP 34/17, all under the terms of the Budapest Treaty.

By reading this disclosure a person skilled in the art is aware that by using the teaching of the present invention it is possible to provide products comprising a microorganism according to the invention as well as carotenoid compound, which can be manufactured more easily and more economically then what is described in the art before. In addition, the use of said microorganisms or carotenoid is a subject matter of the present invention, too.

Accordingly, the present invention also involves a product comprising (a) a microorganism belonging to the photoautotrophic algae of the Class Chlorophyceae, preferably belonging to the Order Volvocales, more preferably to the Family Haematococcaceae, most preferably to the Genus *Haematococcus* which is capable of producing carotenoid, in particular astaxanthin, with a volumetric yield of at least $5.0$ mg$l^{-1}$, preferably of at least $7.0$ mg$^{-1}$, most preferably of at least $8.0$ mg$^{-1}$ after three days of induction of the red phase (carotenogenesis) or within a period of time not substantially exceeding three days of induction of carotenogenesis, comprising the microorganism as a whole or a part thereof, further comprising enrichment products, extracts, centrifugates, isolated or disrupted cells or parts thereof obtainable by chemical, enzymatic or physical treatment, debris of cells, homogenates, lyophilisates, or a mixture thereof, or (b) an isolated carotenoid compound or substance, in particular comprising astaxanthin, obtainable from the said microorganism or parts thereof, being present in a dry state or solved in a liquid or present in an immobilized form, and (c) an adjuvant or an excipient selected from the group consisting of a solid, semi-solid, creamy, powdery, foamy, viscous or liquid material which is in contact with the microorganism of (a) and/or the isolated carotenoid according to (b).

The product may comprise a food product, a feed product, a cosmetic product or a pharmaceutical product.

Preferably, the microorganism, which is most particular useful for manufacturing the said products is selected from the group consisting of strain MS13, strain MC35 and strain MC36, as described supra. These mutants are described in more detail in the Examples.

Likewise, the use of a microorganism according to the invention also pertains to the manufacture of a product. In particular, the present invention also comprises the use of a microorganism belonging to the photoautotrophic algae of the Class Chlorophyceae, preferably belonging to the Order Volvocales, more preferably to the Family Haematococcaceae, most preferably to the Genus *Haematococcus*, which is capable of producing carotenoid, in particular astaxanthin, with a volumetric yield at a rate of at least $5.0$ mg $l^{-1}$ after a period of time of three days of induction of carotenogenesis, the use comprising the microorganism as a whole or a part thereof, further comprising enrichment products, extracts, centrifugates, which is a pellet obtained after centrifugation, isolated cells or parts thereof obtainable by chemical, enzymatic or physical treatment, debris of cells, homogenates, or lyophilisates, or a mixture thereof, for the manufacture of a food product, a cosmetic product, an animal feed or a pharmaceutical or an additive, adjuvant or excipient to a food, to a cosmetic, to a feed or to a pharmaceutical.

The preferred microorganism that can be used for the manufacture of the said products is selected from the group consisting of strain MS13 strain MC35 and strain MC36, as described supra.

Furthermore, the invention is also directed to a microorganism belonging to the photoautotrophic algae having the features i) production of a carotenoid with a volumetric yield at a rate of at least $5.0$ mg $l^{-1}$, preferably of at least $7.0$ mg $l^{-1}$, more preferably of at least $8.0$ mg $l^{-1}$, ii) volumetric yield is obtained after three days of induction of the red phase or within a period of time substantially not exceeding three days of induction of carotenogenesis and iii) constant growth rate within a cell density corresponding to an OD of $0.1$ to $0.4$ at $414$ nm in exponential phase when cultured in a mineral medium at $25°$ C.

In addition, the present invention also relates to the use of a carotenoid, in particular astaxanthin, produced by a microorganism belonging to the photoautotrophic algae of the Class Chlorophyceae, preferably belonging to the Order Volvocales, more preferably to the Family Haematococcaceae, most preferably to the Genus *Haematococcus* which is capable of producing carotenoid, in particular astaxanthin, with a volumetric yield of at least $5.0$ mg $l^{-1}$ after three days of induction of the red phase or within a period of time substantially not exceeding three days of induction of carotenogenesis, which is recoverable or isolatable from the culture medium and/or by extraction from the microorganism or from disrupted cells or parts thereof by chemical, enzymatic or physical methods or by means of centrifugation, homogenisation, evaporation, condensation, concentration or lyophilisation, being present in a dry state or solved in a liquid or present in an immobilized form, for the manufacture of a food product, a cosmetic product an animal feed product or a pharmaceutical product, or as an additive or an adjuvant to a food, a cosmetic, a feed or a pharmaceutical.

It is preferred to use a microorganism, which is selected from the group consisting of strain MS13 strain MC35 and strain MC36 as described supra.

The present invention also deals with a mutant of a microorganism belonging to the photoautotrophic algae of the Class Chlorophyceae, preferably belonging to the Order Volvocales, more preferably to the Family Haematococcaceae, most preferably to the Genus *Haematococcus* which is capable of producing carotenoid, obtainable by mutagenesis and by selection against an agent that inhibit the carotenoid biosynthesis in at least one step of the pathway, which is capable of producing a carotenoid, preferably astaxanthin, with a volumetric yield of at least $5.0$ mg $l^{-1}$ after three days of induction of the red phase or within a period of time substantially not exceeding three days of induction of carotenogenesis.

It is a preferred object of the invention that the said mutant further exhibits a carotenoid volumetric productivity between 1.5-fold and 3.0 fold, preferably between 1.7-fold and 2.8 fold, more preferably between 1.9 and 2.2-fold, with respect to its corresponding wild type microorganisms and that its growth rate is substantially similar to the corresponding wild type microorganism.

In particular, a mutant microorganism, which is selected from the group consisting of strain MS13 strain MC35 and strain MC 36 as described supra, is particular preferred.

A mutant obtainable by any of the methods as described above is also comprised by the present invention.

In order to make further favourable use of the present invention a kit or a kit-of-parts is provided comprising a carotenoid or a carotenoid pigment in isolated, purified, extracted, enriched or immobilized form or a suitable microorganism as described above, useful in the production of a carotenoid, preferably in the production astaxanthin, and/or products and goods containing a carotenoid, preferably astaxanthin, and/or a finished product or a manufactured article, which may or may not contain a carotenoid, preferably astaxanthin, which are contained or packaged spatially separated in one or more containers.

The microorganism as a part of the kit can be available in several forms and conditions. For example on or more containers of the kit may contain the microorganism in form of an aqueous solution, as disrupted cells, as part of cells or as cell debris, in concentrated, accumulated, capsulated or pressed form, for instance as a pellet, capsule, powder, pill, paste, cream or tablet or other suitable galenic formulation such as drugs or sugar coated pills, a lyophilisate, or immobilised on a carrier, surface, substrate, for instance an admixture with starch, a gel, cellulose or derivatives thereof.

The kit or kit-of-parts may consist of at least one container comprising ampoules, flasks, boxes, tins or cans, a medical kit, or a collection or mixture of containers comprising at least one of these parts.

The microorganisms as defined above may be present or packaged in at least one of these containers. In another container an adjuvant or an additive or an excipient in liquid, viscous or solid form known in the art may be present so as to form a kit or kit-of-parts.

Regarding the adjuvants, additives or excipients a person skilled in the art is aware of them and knows their nature and function. Generally, such a substance is inactive and is used as a carrier for an active ingredient for food or of a medication. Accordingly, the carotenoid of the present invention may be dissolved or mixed with an excipient, allowing for convenience consumption or use or accurate dosage. For oral administration or consumption tablets or capsules may be used. However, in cases where the intestinal tract must be bypassed rectal administration by a suppository may be preferred. More particular, the adjuvants, additives and excipients according to the present invention comprises binders such as starches, sugars, cellulose or modified cellulose such as hydroxypropyl cellulose or methyl cellulose, lactose, sugar alcohols like xylitol, sorbitol or manitol, polyethylene glycol, or coatings such as cellulose, zein or other polysaccharides, or lubricants such as stearin, magnesium stearate or stearic acid, or preservatives such as additional antioxidants such as ascorbic acid.

Accordingly, the present invention is also directed to a kit or a kit-of-parts comprising a carotenoid, preferably astaxanthin, consisting a carotenoid-producing mutant microorganism or strain as described above, and/or a product according as described supra, and/or a mutant and/or a microorganism according to the invention and optionally one or more additives, adjuvants or excipients and a container.

The publications and patent applications cited in the present description are incorporated herein by reference.

EXAMPLES

Example 1

Materials and Culture Media

As a starting material the wild type strains of *Haematococcus pluvialis* CCAP 34/8 and SAG 34-1b were used. Strain CCAP 34/8 can be obtained from CCAP strain collection and strain SAG 34-1b can be obtained from SAG Culture Collection and are commercially available.

As culture medium for all strains, as not otherwise indicated, a mineral salt medium was used which was composed as follows (amounts per litre).

1.0 g $NaNO_3$; 0.04 g $Ca(NO_3)_2.4H_2O$; 0.05 g $KH_2PO_4$; 0.049 g $MgSO_4.7H_2O$; 0.01 g $H_3BO_3$; 10 mg $CaCl_2$, 4.5 mg EDTA-FeNa, 4.5 mg $EDTA-Na_2$, 2.8 mg $MnCl_2.4H_2O$; 0.042 mg $ZnCl_2$; 0.04 mg $CoCl_2.6H_2O$; 0.018 mg $(NH_4)_6Mo_7O_{24}$; 0.04 mg $CuSO_4.5H_2O$; 100 ml of a vitamin solution. The vitamin solution contained per liter: 0.2 g biotin, 1.0 g $B_1$ and 0.05 g $B_{12}$. The vitamin solution was sterilized separately by filtration and added before inoculation Example 2

Cell Culture

The preparation of the inoculum was conducted by using the strains described in Example 1.

In 100 ml sterilized mineral medium according to Example 1 cells of one colony of *Haematococcus pluvialis* was taken from agar plate and the cells were cultured at 25° C. in a still culture until an optical density (OD) between 0.1 and 0.3, measured at 414 nm, was achieved The inoculum were added to the mineral medium according to Example 1. After some days (3-5 days) of growth under an irradiance of 70 $\mu Em^2 s^{-1}$ (fluorescent lamp light) and 25° C. of temperature, it was measured the cell density (OD) of the inoculum (mid-exponential phase) and the vegetative stage of the cells was controlled by the microscopic observation. Then, it was calculated the aliquot necessary to have a initial cell density of $5 \times 10^4$ cells per ml, corresponding to an optical density (OD) 0.025, measured at 414 nm, in 20 ml of mineral medium in the new Erlenmeyer flask.

Example 3

Mutagenesis

Cells of the mid-exponential phase culture of Example 2 were harvested by centrifugation at 1900×g. The yield of the cells was $10^8$ cells. The cells were then washed twice with 50 ml sterile water.

The washed cells were harvested by centrifugation at 1900×g and resuspended in 5 ml of sterilized water/medium at room temperature (approx. 25° C.) to obtain a cell suspension of $2 \times 10^7$ cells per ml. In this cell suspension 200 $mgl^{-1}$/or 1.36 mM/or 0.5 ml of solution containing 2000 $mgl^{-1}$ of N-methyl-N'-nitro-nitrosoguanidine (NG) was added. The mutagenesis was performed by exposure of the cells to this NG containing solution during 1 hour at room temperature.

A previous experiment was done to Find the concentration of NG leading to 5-10% and 50% viability to this mutagen. Briefly, this previous experiment was carried out at different concentrations of NG: 10-20-50-100-200-400-500 $mgl^{-1}$ and viability was compared with an experiment carried out in parallel without adding of NG.

The concentration leading to 5-10% viability corresponded to 200 $mgl^{-1}$/or 1.36 mM $mgl^{-1}$ of NG and that leading to 50% viability corresponded to 50 $mgl^{-1}$/or 0.34 mM of NG (for *H. pluvialis* CCAP 34/8 strain).

After the incubation with NG, the cells were washed twice with sterile water and incubated in 20 ml liquid mineral medium as described in Example 1 during 24 hours at low light to allow the cells to recover from damages caused by the mutagen and/or new phenotype expression.

Further selection was conducted as described below.

Example 4

Selection of Mutants

Selection of the mutants obtained in Example 3 was based on the resistance of mutated cells to the three herbicides norflurazon, diphenylamine and nicotine that inhibit the carotenoid biosynthesis at different steps of the pathway. Norflurazon abort the biosynthesis of astaxanthin at the beginning of the pathway. Nicotine is a specific inhibitor of the lycopene β-cyclase and does not allow the conversion of lycopene to β-carotene. Diphenylamine inhibits β-carotene oxygenase, in less extent β-carotene hydroxylase and at higher concentrations (more then 100 μM) also phytoene desaturase. So, when wild type cells are spread on these herbicides containing media, they are blocked in the corresponding enzymes and cannot perform the biosynthesis of astaxanthin. If the cells grow under light conditions, they die, since in the absence of astaxanthin the cells do not have protection from photo-oxidative stress.

The herbicide norflurazon was obtained from SUPELCO Supelco Park, Bellefonte, Pa., USA, diphenylamine and nicotine was obtained from SIGMA, Sigma-Aldrich, Inc., USA.

Before selection has been carried out the minimal concentrations of the herbicides which inhibit the growth of the wild strains were determined. These concentrations were also applied for selection of mutants. The results of *Haematococcus pluvialis* growth inhibition by the herbicides and the concentrations used in the selection experiments are shown in Table 1.

TABLE 1

| Herbicide | *Haematococcus pluvialis* strain | |
|---|---|---|
| | CCAP 34/8 | SAG 34-1b |
| Norflurazon | 3 μM | 2 μM |
| Diphenylamine | 150 μM | 60 μM |
| Nicotine | 400 μM | 500 μM |

In order to select the mutants on the basis of the above mentioned herbicides agar plates were prepared by using 1.5% agar Bacto Agar BD in which different concentrations of the herbicides according to Table 1 were incorporated.

The selection was performed by spreading aliquots of 200 μl of the cell suspension in mineral medium supplemented with herbicide for recovering the cells obtained in Example 3 on the agar plates carrying mutation in corresponding gene of biosynthetic pathway of astaxanthin. The plates were incubated under continuous white light of fluorescent lamps (400-700 nm) of 70-100 μEm$^{-2}$s$^{-1}$ during 3-5 weeks at 25° C.

The first herbicide resistant colonies appeared after 3 to 4 weeks. According to the literature, the frequencies of appearance of herbicide resistant mutants of *Haematococcus pluvialis* are less than 10$^{-7}$ (Tjahjono A. E. et al, Isolation of resistant mutants for a green alga *Haematococcus pluvialis*, and their hybrid formation by protoplast fusion for breeding of higher astaxanthin producers. J. Ferment. Bioeng. 77: 352-357, 1994). However, most surprisingly and in contrast to what is described in the literature the results obtained here were higher and were considerably above 10$^{-7}$.

The following Table 2 shows the frequencies of herbicide resistance mutants formation of *Haematococcus pluvialis* in mutagenesis by NG.

The frequency for nicotine resistant mutant formation at 50% viability was less than for norflurazon and the frequency of mutant formation for both herbicides was less in the case of mutagenesis which produced 50% of viability of the cells than in the case of mutagenesis which produced 5-10% viability of the cells.

Example 5

Purification of the Mutants

The mutants that have been selected by the procedure according to Example 4 were subcultured twice on new agar medium composed as described in Example 4. This was done in order to purify the mutants and to check their resistance to the appropriate herbicide. The subculture was performed as described in Example 4.

Example 6

Analysis of the Mutants

Purified mutant's colonies obtained from Example 5 keeping resistance to the corresponding herbicide were then checked on growth rate in microtiter plates using a Microtiter Plates Rider. For this test the mutants and parental strains as a controls were grown in liquid mineral medium in Erlenmeyer flasks under an irradiance of 70 μm$^2$s$^{-1}$ (fluorescent lamp light) and 25° C. of temperature and the 0.2 ml aliquots were transferred in Microtiter Plates and optical density was measured at 414 nm every day Microtiter Plates Rider (Labsystems iEMS Reader MF).

Only the well growing resistant colonies, that means having about the same growth rate with regards to corresponding wild type strains, were then analysed an astaxanthin accumulation.

For the evaluation of astaxanthin production by the obtained mutants the mutants and the corresponding wild strains were grown in liquid mineral medium in still cultures for 6 days at 25° C. starting at the same cell density (5×10$^4$ cell/ml) regarding the two strains.

In order to analyse many mutants still cultures (20 ml) has been chosen as quick and easy method. The medium of the still culture was the same as set forth in Example 1. The green phase was grown at 70 μE m$^{-2}$s$^{-1}$ for 6 days at 25° C. For the induction of the red phase, the cultures were centrifuged at 1990×g by using a rotor B 2295 and a Megafuge 1.0 Heraeus centrifuge for 3 minutes at room temperature to remove the mineral medium and replace it by the same volume of distilled water, and the cells were illuminated at a higher irradiance (180 μE m$^{-2}$s$^{-1}$). The cells of the red phase were cultured at 25° C. for 3 days.

Three mutants could be selected, which exhibited an increased volumetric astaxanthin yield (mg l$^{-1}$). The mutants were called MS13, this strain having been deposited with the Culture Collection of Algae and Protozoa under the terms of the Budapest Treaty giving accession number CCAP 34/15, MC35, this strain having been deposited with the Culture

TABLE 2

| *Haematococcus* pluvialis strain | Viability 5-10% | | Viability 50% | |
|---|---|---|---|---|
| | Norflurazon | Nicotine | Norflurazon | Nicotine |
| SAG 34-1b | (6.7 ± 6.1) · 10$^{-7}$ | (3.6 ± 2.8) · 10$^{-6}$ | (2.0 ± 1.2) · 10$^{-7}$ | (1.0 ± 0.02) · 10$^{-7}$ |

Collection of Algae and Protozoa under the terms of the Budapest Treaty giving accession number CCAP 34/16 and MC36, this strain having been deposited with the Culture Collection of Algae and Protozoa under the terms of the Budapest Treaty giving accession number CCAP 34/17.

The mutant MS13 came from the mutagenesis of the wild type *Haematococcus pluvialis* SAG 34-1b and the mutants MC35 and MC36 came from the wild type strain *Haematococcus pluvialis* CCAP 34/8. These three mutants were obtained in conditions of mutagenesis giving 5-10% of viability. The mutant MS13 is resistant to nicotine and the mutants MC35 and MC36 are resistant to norflurazon.

Astaxanthin volumetric yield, astaxanthin content per dry weight of the best mutants, as well as growth in terms of dry weight of the wild strains and the three mutants MS13, MC35 and MC36 are shown in Table 3.

TABLE 3

Astaxanthin volumetric yield and dry weight content of the best mutants and the corresponding wild strains

| H. pluvialis strain | Astaxanthin yield (mg l$^{-1}$) 3 days | Astaxanthin yield (mg l$^{-1}$) 6 days | Astaxanthin yield (mg l$^{-1}$) (% relative to the wild strain) 3 days | Astaxanthin yield (mg l$^{-1}$) (% relative to the wild strain) 6 days | Dry weight (g l$^{-1}$) 6 days | Astaxanthin content mg (g dw$^{-1}$) 6 days | Astaxanthin content mg (g dw$^{-1}$) (% relative to the wild strain) 6 days |
|---|---|---|---|---|---|---|---|
| Wild strain CCAP | 4.6 ± 1.0 | 11.8 ± 5.1 | 100 | 100 | 1.22 | 10.6 ± 4.6 | 100 |
| Wild strain SAG | 4.9 ± 1.3 | 10.1 ± 2.9 | 100 | 100 | 1.12 | 9.4 ± 2.7 | 100 |
| MS13 | 9.2 ± 2.8 | 15.2 ± 3.9 | 188 | 150 | 1.12 | 13.5 ± 3.5 | 144 |
| MC35 | 10.3 ± 1.5 | 19.0 ± 3.0 | 224 | 161 | 1.31 | 14.5 ± 2.3 | 137 |
| MC36 | 8.8 ± 2.7 | 17.9 ± 1.6 | 191 | 154 | 1.25 | 14.3 ± 1.3 | 135 |

The data represent the mean value ± standard deviations of 3-6 independent experiments.
"dw" means dry weight.

Both wild strains exhibited about the same astaxanthin volumetric yield, astaxanthin content per dry weight and growth in terms of dry weight. The increase in the volumetric astaxanthin yield (mg l$^{-1}$) in the three selected mutants with regards to the wild strains was higher after 3 days of induction of the red phase, which was performed in distilled water at 25° C., than after 6 days. These results indicate that these three mutants are early accumulators of astaxanthin, which is very interesting for industrial applications. After 3 days of induction of the red phase the mutants MS13, MC35 and MC36 exhibited an astaxanthin volumetric productivity of more than two-fold (1.9 to 2.2 fold) with respect to their corresponding wild strain. After 6 days of induction of the red phase the astaxanthin volumetric productivities were about 50-60% higher than the corresponding parental strains. It is important to remark that these three mutants exhibited similar growth (dry weight) to the corresponding wild strains, which is also important for practical uses.

Example 7

Determination of Volumetric Astaxanthin Yield or Productivity

The aliquots (1 ml) of the cultures recollected after 3 and 6 days of red phase induction were analysed by HPLC/spectrophotometry and the obtained data were recalculated in terms of mg of astaxanthin per 1l of culture.

Example 8

Determination of Astaxanthin Content Per Dry Weight of the Cultures

The aliquots (1 ml) of the cultures recollected after 3 and 6 days of red phase induction were analysed by HPLC/spectrophotometry. At the same time 5-10 ml of the cells culture were recollected, thoroughly washed with distilled water and dried at 80° C. during 2 days. The obtained data of astaxanthin yield (astaxanthin mg l$^{-1}$) were divided per dry weight content (g l$^{-1}$) and to represent the data in terms of Astaxanthin content mg (g·dw$^{-1}$).

Example 9

Preparation of Astaxanthin for Analysis

Aliquots of purified *Haematococcus pluvialis* cells from a culture obtained from Example 5 were harvested by centrifugation (1990×g) for 3 min and washed in distilled water. The cells after centrifugation were broken by aim of mortar and pestle in the presence of aluminium powder and then resuspended in a suitable organic solvent, for instance in acetone. The carotenoid extract was separated from the cell debris by centrifugation at 1900×g, saponificated with a mixture of the same volumes of 2% (w/v) solution of KOH in methanol and diethyl ether, then the supernatant was evaporated under $N_2$ and the pellet was resuspended in acetone, centrifuged at 3300×g and the supernatant containing astaxanthin was used for farther analyses or stored at −20° C. until required later.

What is claimed is:

1. A method for producing astaxanthin using a *Hematococcus pluvialis* micro-organism comprising the steps of:
    (a) culturing in a medium under conditions for induction of carotenogenesis a noraflurazon-resistant mutant of wild-type *Hematococcus pluvialis*, wherein the mutant is capable of producing astaxanthin with a volumetric yield of 1.5-fold to 3.0-fold compared to wild type *Hematococcus pluvialis* within three days of induction of carotenogenesis, and (b) recovering or isolating the astaxanthin from the medium where carotenogenesis was induced,
and/or from the mutant micro-organism or parts thereof, by extraction; and/or by centrifugation; and/or by disrupting isolated cells of the mutant micro-organism or parts thereof by chemical, enzymatic and/or physical treatment; and/or by homogenization of the mutant cells and/or the mutant micro-organism or parts thereof, or from cell debris; and/or by lyophilisation of the mutant micro-organism or parts thereof.

2. The method of claim 1 wherein said norflurazon-resistant mutant is obtained by mutagenesis of the wild type *Hematococcus pluvialis* using a nitrosoguanidine derivative.

3. A method for establishing a mutant strain of *Hematococcus pluvialis* capable of producing astaxanthin in an enhanced level relative to a corresponding wild type strain of *Hematococcum pluvialis*, which method comprises the steps of:
   (a) cultivating the wild type strain in a mineral salt medium,
   (b) harvesting cultivated cells in the exponential growth phase,
   (c) treating the cultivated cells with at least one mutagen,
   (d) exposing the cells to norflurazon, and
   (e) selecting norflurazon-resistant cells capable of producing astaxanthin in a level higher than the wild type strain with a volumetric yield of 1.5-fold to 3.0-fold compared to the wild type strain after three days of induction of carotenogensis or within a period of time not exceeding three days of induction of carotenogenesis and which exhibit similar growth to the wild type strain.

4. The astaxanthin-producing mutant strain of *Hematococcus pluvialis* generated by the method of claim 3.

5. The astaxanthin-producing micro-organism according to claim 4 which is selected from the group consisting of strain MC35 deposited under accession No. CCAP 34116 and strain MC 36 deposited under accession No. CCAP 34/17.

6. A noraflurazon-resistant mutant of *Hematococcus pluvialis* which produces astaxanthin with a volumetric yield of 1.5-fold to 3.0-fold compared to wild type *Hematococcus pluvialis* within three days of induction of carotenogenesis.

7. The mutant of claim 6 which is strain MC35 deposited under accession No. CCAP 34116 or strain MC 36 deposited under accession No. CCAP 34/17.

8. The method of claim 3, wherein the mutagen is a nitrosoguanidine derivative.

9. The method of claim 8, wherein the mutagen is N-methyl-N'-nitro-nitrosoguanidine.

10. The method of claim 8, wherein treatment of the cultivated cells in step (c) results in 5-10% viability.

11. The method of claim 2, wherein the norflurazon-resistant mutant is obtained by mutagenesis of the wild type *Hematococcus pluvialis* using N-methyl-N'-nitro-nitrosoguanidine.

12. The method of claim 1, wherein the volumetric yield is 1.9-fold to 2.2-fold compared to wild type *Hematococcus pluvialis* within three days of induction of carotenogenesis.

* * * * *